United States Patent
Li et al.

(10) Patent No.: US 11,813,238 B2
(45) Date of Patent: Nov. 14, 2023

(54) MEDIUM CHAIN FATTY ACIDS FOR USE IN THE PREVENTION OR TREATMENT OF CARDIAC ENLARGEMENT AND/OR VALVULAR HEART DISEASE

(71) Applicant: SOCIETE DES PRODUITS NESTLE S.A., Vevey (CH)

(72) Inventors: Qinghong Li, Chesterfield, MO (US); Maurice Beaumont, Oran la Ville (CH)

(73) Assignee: Societe des Produits Nestle S.A., Vevey (CH)

(*) Notice: Subject to any disclaimer, the term of this patent is extended or adjusted under 35 U.S.C. 154(b) by 256 days.

(21) Appl. No.: 16/617,668

(22) PCT Filed: May 28, 2018

(86) PCT No.: PCT/EP2018/063958
§ 371 (c)(1),
(2) Date: Nov. 27, 2019

(87) PCT Pub. No.: WO2018/219877
PCT Pub. Date: Dec. 6, 2018

(65) Prior Publication Data
US 2020/0138762 A1   May 7, 2020

Related U.S. Application Data

(60) Provisional application No. 62/512,118, filed on May 29, 2017.

(51) Int. Cl.
| | | |
|---|---|---|
| A61K 31/20 | (2006.01) | |
| A23L 33/12 | (2016.01) | |
| A23L 33/175 | (2016.01) | |
| A23L 33/16 | (2016.01) | |
| A23L 33/15 | (2016.01) | |
| A61P 9/10 | (2006.01) | |
| A61K 31/145 | (2006.01) | |
| A61K 31/198 | (2006.01) | |
| A61K 31/202 | (2006.01) | |
| A61K 31/355 | (2006.01) | |
| A61K 33/06 | (2006.01) | |

(52) U.S. Cl.
CPC ............ *A61K 31/20* (2013.01); *A23L 33/12* (2016.08); *A23L 33/15* (2016.08); *A23L 33/16* (2016.08); *A23L 33/175* (2016.08); *A61K 31/145* (2013.01); *A61K 31/198* (2013.01); *A61K 31/202* (2013.01); *A61K 31/355* (2013.01); *A61K 33/06* (2013.01); *A61P 9/10* (2018.01); *A23V 2002/00* (2013.01)

(58) Field of Classification Search
CPC .... A61K 31/20; A61K 31/145; A61K 31/198; A61K 31/202; A61K 31/355; A61K 33/06; A23L 33/12; A23L 33/175; A23L 33/16; A23L 33/15; A61P 9/10
See application file for complete search history.

(56) References Cited

U.S. PATENT DOCUMENTS

| | | | | |
|---|---|---|---|---|
| 4,920,098 | A | * | 4/1990 | Cotter ................. A61K 9/0029 514/14.9 |
| 9,393,224 | B2 | * | 7/2016 | Hirano .................... A61K 31/19 |
| 2007/0281993 | A1 | * | 12/2007 | Rozen ..................... A61P 31/18 554/1 |
| 2011/0059202 | A1 | * | 3/2011 | Zicker ..................... A61P 33/02 426/2 |
| 2013/0295171 | A1 | * | 11/2013 | Minatelli ............. A61K 31/122 424/453 |

FOREIGN PATENT DOCUMENTS

| | | |
|---|---|---|
| CA | 1318172 | 5/1993 |
| EP | 2749281 | 7/2014 |
| WO | 03015695 A2 | 2/2003 |
| WO | 2015034984 | 3/2015 |
| WO | 2017199223 | 11/2017 |

OTHER PUBLICATIONS

El Camino (2021).*
Pervaiz et al. "MCT oil-based diet reverses hypertrophic cardiomyopathy in a patient with very long chain acyl-coA dehydrogenase deficiency" Indian J Hum Genet., 2011, vol. 17, No. 1, pp. 29-32.
Ismael, Saifudeen "Metabolic Modulation by Medium Chain Triglycerides Prevents Cardiac Remodeling in Spontaneously Hypertensive Rat" Ph.D. Thesis, Jan. 1, 2015, pp. 1-198.
Doi et al. "Milder childhood form of very long-chain acyl-CoA dehydrogenase deficiency in a 6-year-old Japanese boy" Eur J Pediatr, 2000, vol. 159, pp. 908-911.
Saifudeen et al., "Metabolic Modulation by Medium-Chain Triglycerides Reduces Oxidative Stress and Ameliorates CD36-Mediated Cardiac Remodeling in Spontaneously Hypertensive Rat in the Initial and Established Stages of Hypertrophy", Journal of Cardiac Failure, vol. 23, Issue No. 3, 2017, pp. 240-251.
Akira, "Echocardiography", vol. 9, Issue No. 11, 2008, pp. 1086-1098.
"Pediatrics", vol. 77, 2014, pp. 353-354.
Japan Patent Office Communication for Application No. JP2019-565906, Dispatch No. 285529, Dispatch Date Jun. 21, 2022, 8 pages.
European Patent Office Communication for Application 18728346.0-1112, dated Apr. 21, 2022, 5 pages.

* cited by examiner

*Primary Examiner* — Shirley V Gembeh
(74) *Attorney, Agent, or Firm* — K&L Gates LLP (57) ABSTRACT

Medium chain fatty acids or a composition comprising medium chain fatty acids for use in the prevention or treatment of cardiac enlargement, valvular heart disease and/or a condition associated with either of the foregoing in a human.

16 Claims, 5 Drawing Sheets

MEDIUM CHAIN FATTY ACIDS FOR USE IN THE PREVENTION OR TREATMENT OF CARDIAC ENLARGEMENT AND/OR VALVULAR HEART DISEASE

CROSS REFERENCE TO RELATED APPLICATIONS

The present application is a National Stage of International Application No. PCT/EP2018/063958, filed on May 28, 2018, which claims priority to U.S. Provisional Patent Application No. 62/512,118, filed on May 29, 2017, the entire contents of which are being incorporated herein by reference The present invention relates to medium chain fatty acids or a composition comprising medium chain fatty acids for use in the prevention or treatment of cardiac enlargement and/or valvular heart disease and/or a condition associated with either of the forgoing in a subject.

BACKGROUND

The role of the heart is to pump blood around the body so as to ensure an optimum supply of oxygen and nutrients to all tissues. If the heart does not pump as efficiently as it should, then this supply of oxygen and nutrients may be compromised. In case of cardiac failure where the efficiency of the heart in providing the tissues with oxygen and nutrients is compromised, failure of other organs and sudden death can ensue.

Abnormal cardiac enlargement and valvular heart disease are both conditions that can negatively affect the heart's ability to pump blood around the body.

Treatments for abnormal cardiac enlargement and/or valvular heart disease usually focus on treating the underlying cause(s) and/or on easing contributing factors. Due to the risk, surgery is often seen as a last resort and medicines such as diuretics, angiotensin-converting enzyme (ACE) inhibitors and beta-blockers are primarily administered. However, these medications can have side effects, moreover, the risk of said side effects may increase as dosages are increased, which may be necessary over time as conditions or symptoms worsen, or as the body builds up a tolerance to the effects of the medication. Accordingly, there is a need to find alternatives to currently used medications that can be used alone or even in combination with these known medications to prevent or treat cardiac enlargement and/or valvular heart disease and/or conditions associated with either of the foregoing in a subject.

Surprisingly the inventors have now found that a composition comprising medium chain fatty acids (herein after MCFAs) may improve (decrease) heart size, and/or improve (increase) blood flow/pumping in the heart of mammals, and may therefore be effective in the prevention and/or treatment of cardiac enlargement and/or valvular heart disease and/or a condition associated with any of the foregoing in a human subject.

SUMMARY OF THE INVENTION

The invention is set out in the claims and in the detailed description included herein.

The present invention provides MCFAs or a composition comprising MCFAs for use in the prevention or treatment of cardiac enlargement and/or valvular heart disease and/or a condition associated with either of the foregoing in a subject wherein, said subject is a human.

The valvular heart disease may be selected from the group consisting of mitral valve insufficiency, aortic valve insufficiency, or tricuspid valve insufficiency. However, the MCFAs or composition comprising MCFAs may be particularly effective in the prevention or treatment of mitral valve insufficiency.

Cardiac enlargement and/or valvular heart disease may affect heart function. This can lead to associated conditions. Particular condition associated with cardiac enlargement and/or valvular heart disease may be thrombosis, hypertension or high blood pressure, irregular heart rhythms, angina, heart attack, heart failure, and cardiac arrest.

The MCFAs may be any MCFAs. Particularly effective MCFAs may be C6:0, C8:0, C10:0, C12:0, and any combination thereof. The MCFAs may be employed in any form suitable for consumption by a subject e.g. monoacylglycerides, diacylglycerides, triacylglycerides, or any combination thereof. It may be particularly effective if the MCFAs are employed, or predominately employed, in the form of triacylglycerides. The triacylglycerides may be in the form, or predominately in the form, of medium chain triglycerides. Medium chain triglycerides may be particularly effective as each triglyceride can deliver up to 3 MCFAs.

The MCFAs or composition comprising MCFAs may be administered for any period of time and may for example be administered for a period of more than 3 months or more than 6 months.

The MCFAs or composition comprising MCFAs may be administered to a human subject at risk of cardiac enlargement and/or valvular heart disease, for example a subject having high blood pressure or hypertension, hypertrophic cardiomyopathy, heart muscle inflammation, myocarditis, thyroid disease, or a disease of the heart valve and/or having had a heart attack or cardiac infarction. The MCFAs or composition comprising MCFAs may be particularly effective in these subjects.

Adults are more likely to suffer from cardiac enlargement and/or valvular heart disease and conditions that increase the risk of cardiac enlargement and/or valvular heart disease. Also these conditions may be age related. Accordingly, the subject may be a human adult, and the cardiac enlargement and/or valvular heart disease may be age-related.

The MCFAs may be administered to a subject simultaneously, sequentially or separately to a medicine intended to treat and/or prevent cardiac enlargement and/or a condition associated therewith and/or a condition that increases the risk of cardiac enlargement and/or valvular heart disease in a subject. Examples of such medicines may be anti-thrombotics, anticoagulants, diuretics, ACE inhibitors, angiotensin-2 receptor blockers, calcium channel blockers, beta blockers, digoxin, amiodarone, anti-arrhythmics, and any combination of the foregoing. Administration of the MCFAs or composition comprising MCFAs may enable the dosage of the medicine to be reduced.

Administration of the MCFAs or composition comprising MCFAs with other ingredients may improve the effectiveness of the MCFAs or composition comprising MCFAs. A composition comprising MCFAs may for example further comprises an omega-3 fatty acid, vitamin E, magnesium, taurine, lysine, a sulfur containing amino acid, carnitine, and mixtures of any of the foregoing. The omega-3 fatty acid may be eicosapentaenoic acid (EPA), docosahexaenoic acid (DHA) and mixtures thereof. The sulfur containing amino acid may be methionine, cysteine, and mixtures thereof.

The composition comprising MCFAs may be any composition suitable for consumption by a subject. It may for example be a medicament, a food product, a beverage, a medical food, an oral nutritional supplement, a nutritional composition, or a supplement to a food product.

As would be evident to the skilled person, the MCFAs or composition comprising MCFAs may be used in the manufacture of a composition for use in the treatment and/or prevention of a cardiac enlargement and/or valvular heart disease and/or a condition associated with any of the foregoing in a subject. They may also be used in a method of treating and/or preventing cardiac enlargement and/or valvular heart disease and/or a condition associated with either of the foregoing in a subject, said method comprising administering to said subject said MCFAs or composition comprising MCFAs, optionally said method can include the step of identifying a subject suffering from or at risk of suffering from cardiac enlargement and/or valvular heart disease and/or a condition associated with either of the foregoing in a subject.

DETAILED DESCRIPTION

In a first aspect of the present invention there is provided MCFAs or a composition comprising MCFAs for use in the prevention or treatment of cardiac enlargement, valvular heart disease and/or a condition associated with either of the foregoing in a subject.

The term subject as used herein refers to a human.

The term "cardiac enlargement" as used herein refers to an abnormal (pathological) increase in the size of the heart. This abnormal enlargement may be because of hypertrophy (an increase in the thickness of the heart muscle) and/or dilation (an increase in the size of the cavity of a chamber of the heart). Cardiac hypertrophy can occur because of any condition that puts the heart under increased stress. The increased stress causes the heart to work harder and the muscle to thicken. Cardiac dilation can occur because of any condition that damages the heart muscle. This is because the heart response to damage can be too thin and stretch out the muscle. As the heart muscle thickens, or thins and stretches, it can become functionally less effective. Cardiac dilation may also occur because of back flow of blood into a heart chamber, for example due to a valvular heart disease. Over the time, the heart muscle becomes dilated to accomodate extra blood.

The term "valvular heart disease" as used herein refers to any abnormal functioning in any of the four heart valves (the mitral, aortic, tricuspid, or pulmonary). The abnormal functioning can increase the stress on the heart (causing it to work harder) and/or can cause damage e.g. infarction because of insufficient supply in blood. Abnormal functioning in any of the valves may be caused by valvular stenosis or valvular insufficiency/regurgitation. In valvular stenosis the valve is abnormally narrow. This, for example, can occur because of a build-up of calcified deposits, or from an infection with rheumatic fever. In valvular insufficiency/regurgitation the valve does not close properly causing blood to leak back into the ventricle from which it is being pumped, for example, in the event of mitral valve insufficiency or mitral disease, blood leaks back into the left atrium (aka mitral regurgitation).

As used herein, the term "valvular insufficiency" refers to any valvular malfunction for example it may refer to valvular regurgitation.

In an embodiment of the invention the valvular heart disease is caused by valvular insufficiency/regurgitation and the valvular heart disease is selected from the group consisting of mitral valve insufficiency/regurgitation, aortic valve insufficiency/regurgitation, or tricuspid valve insuffi- ciency/regurgitation. In a more specific embodiment the valvular heart disease is mitral valve insufficiency/regurgitation.

A variety of health problem/conditions are associated with cardiac enlargement and/or valvular heart disease. This is because the heart muscle is functionally less effective.

In an embodiment of the invention, the conditions associated with cardiac enlargement and/or valvular heart disease are selected from the group consisting of thrombosis, irregular heart rhythms, angina, heart attack, high blood pressure or hypertension, cardiac arrest, and heart failure.

Prevention and/or treatment of conditions associated with cardiac enlargement and/or valvular heart disease may be via the prevention and/or treatment of cardiac enlargement and/or valvular heart disease which prevents the heart muscle becoming functionally less effective.

The term "medium chain fatty acids" as used herein refers to one or more compounds of formula (I), including mixtures of compounds of formula (I)

(I)

wherein, R1 is a C5 to C11 branched or unbranched acyclic alkyl or acyclic alkenyl group; for example R1 is a C5 to C11 unbranched acyclic alkyl group.

In an embodiment of the invention the MCFAs are selected from the group consisting of C6:0 (caproic acid), C8:0 (caprylic acid), C10:0 (capric acid), C12:0 (lauric acid), and any combination thereof.

In an embodiment the MCFAs are a mixture of C6:0, C8:0, C10:0, and C12:0. In a more specific embodiment the MCFAs are a mixture of C6:0, C8:0, C10:0, and C12:0 wherein C8:0 and/or C10 are the dominant MCFAs e.g. wherein more than 30% of the MCFAs are C8:0 or C10:0 for example 30 to 60% are C8:0 or C10:0.

The MCFAs may be employed in any form suitable for consumption by a subject. In an embodiment the MCFAs are employed in the form of monoacylglycerides (hereinafter "MAG"), diacylglycerides (herein after "DAG"), triacylglcerides (hereinafter "TAG"), or any combination thereof.

The term "MAG" as used herein refers to a compound of formula (II) (a glycerol molecule) wherein, one of the OH groups is modified to form an ester bond with an MCFA.

(II)

The term "DAG" as used herein refers to a compound of formula (II) (a glycerol molecule) wherein two of the OH groups are modified to form ester bonds with fatty acids and wherein at least one of the fatty acids that has formed an ester bond with one of the OH groups is a MCFA.

The term "TAG" as used herein refers to a compound of formula (II) (a glycerol molecule) wherein three of the OH groups are modified to form ester bonds with fatty acids and wherein at least one of the fatty acids that has formed an ester bond with one of the OH groups is an MCFA.

It may be particularly beneficial if the MCFAs are employed in the form, or mainly in the form, of TAGs wherein two or three of the fatty acids that have formed ester bonds with the OH groups are MCFAs. Such compounds are called Medium chain triglycerides (hereinafter "MCT").

In an embodiment the MCFAs are employed or comprised in the composition of the invention in the form of TAGs, or predominately (e.g. at least 50%, at least 90%, at least 98%) in the form of TAGs, that are MCTs, or predominantly (e.g. at least 50%, at least 90%, at least 98%) are MCTs.

MCTs may be prepared by any known process, such as direct esterification, rearrangement, fractionation and/or transesterification. A mixture of MCT (MCTs comprising different MCFAs) may, for example, be prepared from a source of vegetable oil, such as coconut oil, through a rearrangement process. The chain length and distribution of the MCFAs included in the MCT mix may vary depending on the source oil. For example, a mixture of MCTs containing 1-10% C6, 30-60% C8, 30-60% C10 and 1-10% C12 can be derived from palm oil and/or coconut oil.

In an embodiment of the present invention the MCFAs employed or comprised in the composition of the invention are TAGs that are MCTs, or predominately MCTs, that are at least in part from coconut oil e.g. more than 50%, more than 60%, or more than 90% from coconut oil.

MCT Mixtures comprising MCTs with about 50% total C8:0 and/or about 50% total C10:0 may be particularly beneficial for use in the invention.

In an embodiment the MCFAs or MCFAs comprised in the composition are in the form of MCT wherein said MCT is a mix of MCTs containing at least about 95% C8:0. The remainder of the fatty acids may be C6:0 and C10:0.

MCTs containing at least about 95% C8:0 can be made by semi-synthetic esterification of octanoic acid to glycerin.

A composition comprising MCFAs in accordance with the invention may comprise lipids consisting essentially of MCTs.

A composition comprising "lipids consisting essentially of MCT" comprises MCTs as at least 20% of the total lipids in the composition, in some embodiments at least 30% of the total lipids in the composition, in other embodiments at least 40% of the total lipids in the composition, and in some embodiments at least 50% of the total lipids in the composition.

The term "prevent" as used herein refers to the prevention of the occurrence, or the reduction of the risk of the occurrence, of a condition in a subject. Prevention can be patient or doctor related.

The term "treat" as used herein refers to the amelioration and/or the alleviation of a condition. The amelioration and/or alleviation may be with respect to one or more symptoms of a condition. The term "treat" may for example refer to a reduction in the severity of a condition and/or in one or more symptom of a condition in a subject. The term "treat" may also refer to slowing the development or progress of a condition. The term does not necessarily imply that a subject is treated until total recovery. Treatment can be patient or doctor related.

Symptoms of cardiac enlargement and/or valvular heart disease are shortness of breath, coughing, heart murmurs, chest discomfort or pain, palpitation, fluid retention in the feet, ankles, or legs, dizziness or light headedness, fatigue, decreased physical capacity, and loss of consciousness. These symptoms may only occur on exertion if the cardiac enlargement and/or valvular heart disease is mild. The MCFAs or composition comprising MCFAs may ameliorate or alleviate one or more of these symptoms.

The relative terms "improved," "increased," "enhanced" and the like refer to the effects MCFAs or a composition comprising MCFAs as disclosed herein on cardiac enlargement and/or valvular heart disease and/or a condition associated with either of the foregoing in a subject in comparison to a subject that is not treated with said MCFAs or composition comprising MCFAs. Said improvement may on a symptom of one of the symptoms of cardiac enlargement and/or valvular heart disease. It is well within the purview of the skilled person to assess an improvement, increase or enhancement.

The MCFAs or composition comprising MCFAs can be administered in any therapeutically effective amount.

As used herein the term "therapeutically effective amount" refers to an amount of the "active" (here, MCFAs, or a composition comprising MCFAs) that prevents and/or treats cardiac enlargement and/or valvular heart disease and/or a condition associated with either of the foregoing in a subject.

Typically, an effective amount will depend on the type, age, size and severity of the condition, on the subject's lifestyle, as well as on its genetic heritage. The effective amount may also depend on the form employed e.g. if the MCFAs are employed in the form of MCTs or comprised in a composition as MCTs.

It is well within the purview of the skilled person to determine an effective amount. An effective amount may, for example, be determined by evaluating the effect of the administration of MCFAs or composition comprising MCFAs on cardiac enlargement and/or valvular heart disease and/or a condition associated therewith in a subject. Such an effect may for example be determined using echocardiography.

An effective amount of MCTs may be 1 g to 40 g per day for example 1 g to 35 g, 5 g to 30 g, 10 g to 20 g per day.

The effective amount may be administered all at once or it may be spread out over several administrations throughout a day. Administration may be by any known method, for example it may be enteral e.g. oral.

The MCFA, or composition comprising MCFA, may be particularly effective if it is administered for a period of time of more than 1 month.

In an embodiment of the invention the MCFAs or composition comprising MCFAs are administered for more than 3 months or more than 6 months.

Non limiting examples of period longer than 3 months include 2, 3, 4, 5, and 6 months.

Non limiting examples of period longer than 6 months include 7, 8, 9, 10, 11, and 12 months.

In another embodiment of the invention the subject is a human at risk of cardiac enlargement and/or valvular heart disease. Any condition that increases stress in the heart and causes the heart to work harder can raise the risk of cardiac enlargement and/or valvular heart disease.

In a more specific embodiment the subject at risk of cardiac enlargement and/or valvular heart disease has high blood pressure or hypertension, hypertrophic cardiomyopathy, heart muscle inflammation, myocarditis, thyroid disease, or a disease of the heart valve and/or may have had a heart attack or cardiac infarction.

The composition of the invention may be used in any human i.e. infant, child or adult. However, cardiac enlargement and valvular disease and/or conditions associated with either of the foregoing are more common in adults. As are conditions that raise the risk of cardiac enlargement and/or valvular heart disease. Accordingly, the composition may be particularly applicable for this group. Accordingly, in an embodiment of the invention, the subject is a human adult.

The term adult as used herein refers to a human of more than 16 years of age, and more specifically a human more than 18 years of age.

Further to the above, the cardiac enlargement and valvular disease or condition associated therewith may be age related. As humans age changes in the heart and blood vessels occur. These changes can result in cardiac enlargement and/or valvular disease. In another embodiment of the invention the subject is a human adult and the cardiac enlargement and/or valvular disease and/or condition associated therewith is age related.

The human adult may be an aging human and may be at least 50 years old, at least 60 years old, at least 70 years old, at least 80 years old.

In an embodiment of the invention MCFAs or composition comprising MCFAs are administered simultaneously, sequentially or separately to a medicine intended to treat and/or prevent cardiac enlargement and/or a condition associated therewith and/or a condition that increases the risk of cardiac enlargement and/or valvular heart disease.

In a more specific embodiment said medicine is selected from the group consisting of an antibiotic, an anti-thrombotic, an anticoagulant, a diuretic, an ACE inhibitor, an angiotensin-2 receptor blocker, a calcium channel blocker, beta blockers, digoxin, anti-arrhythmics, and any combination of the foregoing.

Employing MCFAs or composition comprising MCFAs in combination with a medicine intended to treat and/or prevent cardiac enlargement and/or a condition associated therewith and/or a condition that increases the risk of cardiac enlargement and/or valvular heart disease, may enable the dosage of said medicine to be decreased.

MCFAs or composition comprising MCFAs may also be used in combination with a left ventricular assist device, a pace maker, and/or an implantable cardioverter-defibrillator.

MCFAs or a composition comprising MCFAs may also be used in combination with sodium restriction. The restriction may be mild, moderate, or severe.

In humans; a mild restriction may be a restriction to approximately 3000-4000 mg of sodium per day. This type of restriction is often referred to as a "No Added Salt" or "NAS" diet. A moderate restriction may be approximately 2000 mg of sodium per day and a severe restriction may be approximately 500 mg of sodium per day.

When the MCFAs or composition comprising MCFAs is used in combination with a sodium restriction diet, it may have an improved effect in terms of preventing and/or treating cardiac enlargement and/or valvular heart disease and/or a condition associated with either of the foregoing.

In an embodiment, the MCFAs or its composition comprising MCFAs is used in combination with sodium restriction.

In an embodiment of the present invention the composition comprising an MCFA comprises one or more of the following ingredients: omega-3 fatty acids, Vitamin E, magnesium, carnitine, taurine, lysine, and/or sulfur-containing amino acids. MCFAs or a composition comprising MCFAs may also be administered sequentially, simultaneously or separately to one or more of these ingredients.

When the composition comprising MCFAs also comprises one or more of these additional ingredients, or when MCFAs or composition comprising MCFAs are administered sequentially, simultaneously or separately to one or more of these ingredients, said MCFAs or composition comprising MCFAs may have an improved effect in terms of preventing and/or treating cardiac enlargement and/or valvular heart disease and/or a condition associated with either of the foregoing.

Non-limiting examples of suitable omega-3 fatty acids include eicosapentaenoic acid (EPA), docosahexaenoic acid (DHA), alpha-linolenic acid (ALA) and mixtures thereof.

In an embodiment of the present invention the omega-3 fatty acid is selected from the group consisting of eicosapentaenoic acid (EPA), docosahexaenoic acid (DHA) and mixtures thereof.

The omega-3 fatty acids may be administered in the form of fish oil.

In an embodiment, the omega-3 fatty acids are administered in the form of fish oil. The fish oil may for example be administered in, or added to the composition in, an amount that would equate to a daily intake of fish oil of up to 40 g for example up to 30 g, up to 20 g, up to 10 g, up to 5 g, up to 1 g, up to 500 mg, for example, 500 mg to 40 g, 500 mg to 20 g, 1 g to 30 g, 5 g to 20 g.

In an embodiment, the omega-3 fatty acids are DHA and EPA. The EPA may for example be administered in, or added to the composition in, an amount that would equate to a daily intake of up to 3 g for example up to 2 g, up to 1 g, up to 500 mg, up to 250 mg, up to 200 mg, for example, 200 mg to 2 g, 200 mg to 1 g, 200 mg to 250 mg, 1 g to 3 g. The DHA may for example be administered in, or added to the composition in, an amount that would equate to a daily intake of up to 3 g for example up to 2 g, up to 1 g, up to 500 mg, up to 250 mg, up to 200 mg for example, 200 mg to 2 g, 200 mg to 1 g, 200 mg to 250 mg, 1 g to 3 g.

In an embodiment methionine and/or cysteine may be, administered in, or added to the composition in, an amount that would equate to a combined total daily intake of up to 16 g for example up to 10 g, up to 5 g, up to 10 g, up to 5 g, up to 2 g, up to 1 g, up to 500 mg, for example, 500 mg to 10 g, 500 mg to 5 g, 1 g to 10 g, 1 g to 2 g, 500 mg to 2 g.

In an embodiment lysine may be administered in, or added to the composition in, an amount that would equate to a total daily intake of up to 20 g for example up to 10 g, up to 5 g, up to 10 g, up to 5 g, up to 2 g, up to 1 mg, up to 500 mg, for example 500 mg to 10 g, 500 mg to 5 g, 1 g to 10 g, 500 mg to 2 g.

In an embodiment taurine may be administered in, or added to the composition in, an amount that would equate to a total daily intake of up to 2 g for example up to 1 g, up to 500 mg, up to 100 mg, up to 50 mg, up to 20 mg, for example, 20 mg to 2 g, 50 mg to 1 g, 50 mg to 500 mg, 20 mg to 100 mg.

In an embodiment vitamin E may be administered in, or added to the composition in, an amount that would equate to a total daily dose of up to 600 IU for example up to 500 IU, up to 400 IU, up to 300 IU, up to 200 IU, up to 100 IU, up to 50 IU, up to 20 IU, for example 20 IU to 500 IU, 50 IU to 400 IU, 100 IU to 300 IU.

In an embodiment magnesium may be administered in, or added to the composition in, an amount that would equate to a total daily intake of up to 2 g for example up to 1 g, up to 500 mg, up to 350 mg, up to 200 mg, up to 100 mg up to 50 mg, for example, 50 mg to 2 g, 50 mg to 1 g, 50 mg to 350 mg, 100 mg to 350 mg.

In an embodiment carnitine may be administered in, or added to the composition in, an amount that would equate to a total daily intake of up to 5 g for example up to 4 g, up to 2.5 g, up to 1 g, up to 500 mg, up to 100 mg up to 50 mg, for example, 50 mg to 4 g, 50 mg to 2.5 g, 100 mg to 1 g, 500 mg to 4 g.

As would be evident to the skilled person the amount of an ingredient e.g. DHA, EPA, magnesium, carnitine, taurine, lysine, methionine and/or cysteine, comprised in a composition may depend on how often the composition should be consumed e.g. once per day, twice per day, 4 times per day.

The omega-3 fatty acids may be present in the composition in a concentration of at least about 0.2 wt %, at least about 0.5 wt %, at least about 0.7 wt %, at least about 1.0 wt %, or at least about 2.0 wt %. In an embodiment, the omega-3 fatty acids can range from about 0.2 wt % to about 3 wt % of the composition.

The magnesium may be present in the composition in a concentration of at least about 0.1 wt %, for example at least about 0.15 wt %.

The lysine may be present in the composition in a concentration of at least about 2 wt %, for example at least about 2.5 wt %.

The vitamin E may be present in the composition in a concentration of at least about 1 IU/g, For example at least about 2 IU/g.

The methionine and/or cysteine may be present in the composition in a combined concentration of at least about 2 wt %, for example at least 2.5 wt %.

The taurine may be present in the composition in a combined concentration of at least about 0.2 wt %, for example at least 0.4 wt %.

Non-limiting examples of suitable sulfur-containing amino acids include methionine, cysteine, homocysteine, taurine and mixtures thereof.

The composition comprising MCFAs may also comprise any conventional ingredients traditionally included in compositions for human consumption e.g. food additives, for example one or more proteins, carbohydrates, fats, acidulants, thickeners, buffers or agents for pH adjustment, chelating agents, colorants, emulsifiers, excipients, flavor agents, minerals, osmotic agents, pharmaceutically acceptable carriers, preservatives, stabilizers, sugars, sweeteners, texturizers and/or vitamins, protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents, pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. The ingredients can be added in any suitable amount.

The composition may be any type of composition suitable for human consumption. In an embodiment of the invention the composition comprising MCFAs are selected from the group consisting of a beverage, a medicament, a food product, a medical food, an oral nutritional supplement, a nutritional composition, or a supplement to a food product.

A medical food product is specially formulated and intended for the dietary management of diseases or medical conditions (e.g., to prevent or treat undesirable medical conditions). A medical food product can provide clinical nutrition, for example fulfilling special nutritional needs of patients with a medical condition or other persons with specific nutritional needs. A medical food product can be in the form of a complete meal, part of a meal, as a food additive, or a powder for dissolution.

A food product, medical food or nutritional composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

A supplement may for example be in the form of tablets, capsules, pastilles or a liquid e.g. an MCT oil. The supplement can be added in a product acceptable to the consumer as an ingestible carrier or support. Non-limiting examples of such carriers or supports are a pharmaceutical, a food composition. Non-limiting examples for food compositions are milks, yogurts, curds, cheeses, fermented milks, milk-based fermented products, fermented cereal based products, milk-based powders, human milks, preterm formulas, infant formulas, oral supplements, and tube feedings.

In another aspect of the present invention there is provided MCFAs or a composition comprising MCFAs for use in the manufacture of a composition for use in the treatment and/or prevention of a cardiac enlargement and/or valvular heart disease and/or a condition associated with any of the foregoing in a subject.

In another aspect of the present invention there is provided a method of treating and/or preventing cardiac enlargement and/or valvular heart disease and/or a condition associated with either of the foregoing in a subject, said method comprising administering to said subject MCFAs or a composition comprising MCFAs, optionally said method includes the step of identifying a subject suffering from or at risk of suffering from cardiac enlargement and/or valvular heart disease and/or a condition associated with either of the foregoing in a subject.

In another aspect of the present invention there is provided a composition comprising MCT and one or more of omega 3 fatty acids, lysine, methionine, cysteine, magnesium sulfate, vitamin E, taurine.

In an embodiment, the omega 3 fatty acids are EPA and/or DHA.

In an embodiment the MCT contains MCTs with more than 40% total C8 and more than 50% total C10.

In an embodiment there is provided a composition comprising MCT, DHA, EPA, lysine, methionine, cysteine, magnesium sulfate, vitamin E, taurine wherein, the MCT contains MCTs with more than 40% total C8 and more than 50% total C10.

In an embodiment, the composition comprises at least 5 wt % MCT, at least 0.3 wt % of DHA, at least 0.4% of EPA, at least 2 wt % of lysine, at least 2 wt % of methionine and cysteine combined, at least 0.15 wt % of magnesium, at least 0.9 IU/g of vitamin E, and at least 0.2% of taurine wherein, the MCT contains MCTs with more than 40% total C8 and more than 50% total C10.

The composition is suitable for consumption for a human, In an embodiment the composition may not be a pet food.

It should be appreciated that all features of the present invention disclosed herein can be freely combined and that variations and modifications may be made without departing from the scope of the invention as defined in the claims. Where known equivalents exist to specific features, such equivalents are incorporated as if specifically referred to in this specification. Furthermore, it should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

As used in this disclosure and the appended claims, the singular forms "a," "an" and "the" include plural referents unless the context clearly dictates otherwise. Thus, for example, reference to "an ingredient" or "the ingredient" includes two or more ingredients. The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within-5% to +5% of the referenced number, more preferably within-1% to +1% of the referenced number, most preferably within-0.1% to +0.1% of the referenced number. A range that is "between" two values includes those two values. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition unless expressed otherwise. When reference is made to the pH, values correspond to pH measured at 25° C. with standard equipment.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Moreover, the description of some steps as "optional" does not imply that the other steps which are not explicitly described as optional are necessarily required.

There now follows a series of non-limiting examples that serve to illustrate the invention.

EXAMPLES

Example 1

By way of example and not limitation, the following non-limiting study is illustrative of compositions and methods using MCTs for cardiac protection and treatment of degenerative mitral valve disease (DMVD) in dogs, in one or more embodiments provided by the present disclosure.

Example 1

Cardiac Health Blend (cardiac protection blend (CPB)) Study for Canines with DMVD 19 healthy dogs and 21 with cardiac murmurs were selected for a 6-month study. All dogs were examined by a board-certified veterinary cardiologist using echocardiography and were confirmed as either healthy or having early stage DMVD. Dogs in each group were randomized by age, gender, breed, body weight, and murmur grades into two dietary treatment groups. The control diet provides complete and balanced nutrition manufactured by the Nestle Purina PetCare Company to meet or exceed the requirements as defined by the Association of American Feed Control Officials (AAFCO). The test diet contained all the ingredients in the control diet with the following additional ingredients: medium chain triglycerides (MCTs) in an amount of 5.000 wt %, omega-3 fatty acids in an amount of 0.7489 wt %, lysine in an amount of 2.3000 wt %, methionine and cysteine in an amount of 2.1000 wt %, magnesium sulfate in an amount of 0.1500 wt %, vitamin E in an amount of 0.9206 IU/g, and taurine in an amount of 0.2162 wt %. In the DMVD group, there were 10 dogs in the control diet group and 11 in the test diet group, while in the healthy group, there were 9 in the control diet group and 10 in the test diet group.

Dogs were individually fed to maintain their body weights. Energy intake for maintenance (MER) was estimated using the equation: $MER=139*BW^{0.67}$ (kilocalories), where BW is the body weight of the dog in kilograms. Dogs were weighed weekly and their amount of food offered was increased or decreased by 5% if their BW decreased or increased more than 5% over their initial BW, respectively. Echocardiographic parameters were measured by the cardiologist at the baseline, 3-month, and 6-month post treatment. Dogs received routine healthcare by the staff veterinarians. One DMVD dog of the control diet group was removed after 3 months due to health issues.

Figure 1:
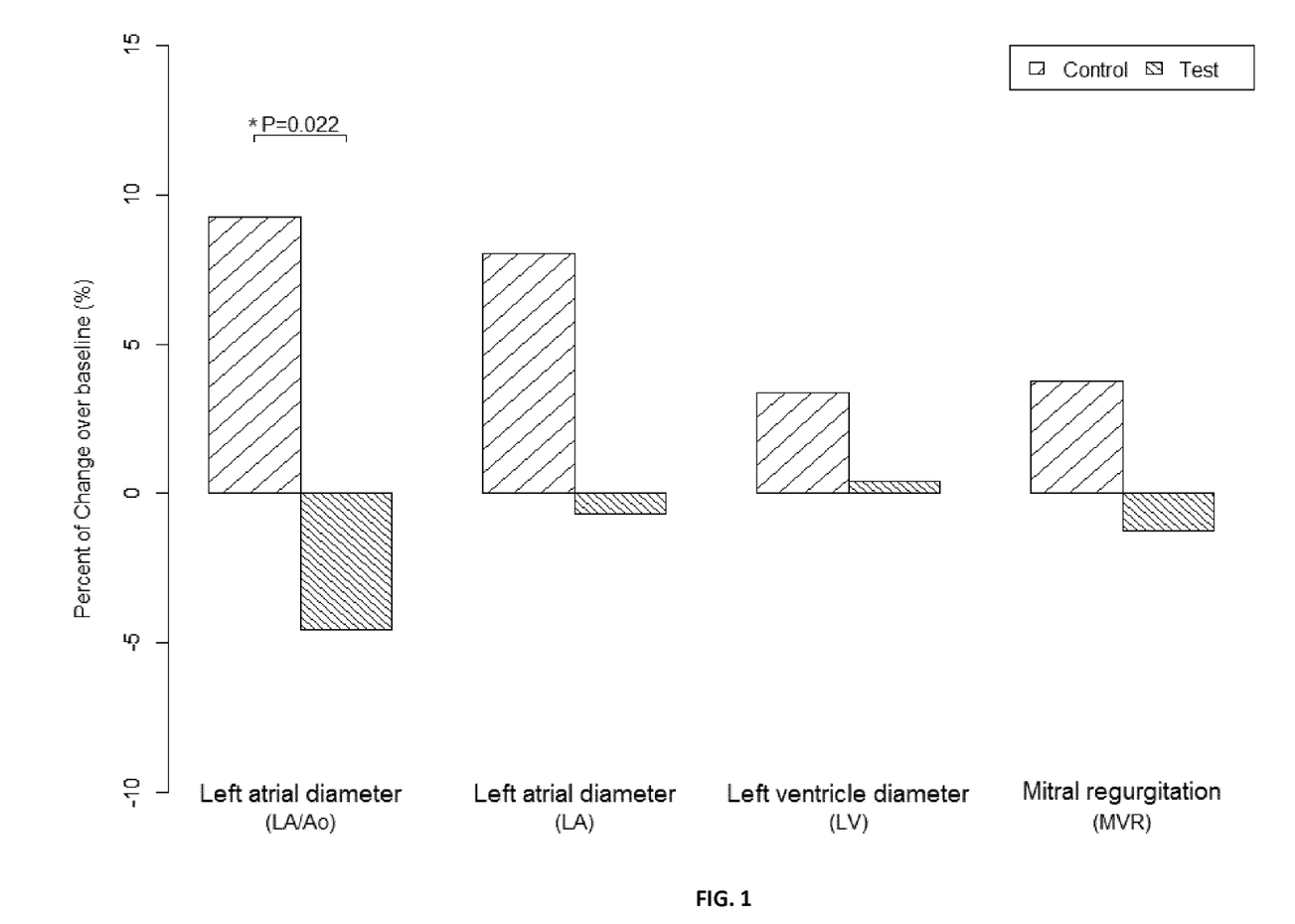
FIG. 1 is a graph of various cardiac measurements for dogs with cardiovascular disease in accordance with one embodiment of the present disclosure.

As shown in FIG. 1, echocardiograms were performed at baseline, 3 months, and 6 months post treatment. Changes between 3 months and baseline in the 4 cardiac measurements, left atrial to aortic root ratio (LA/Ao), left atrial diameter (LA), and left ventricular diameter (LV), and mitral regurgitation rate (MVR), were calculated. Mann-Whitney U test was performed to compare the differences between dogs fed control diet and dogs fed MCT diet and P values were obtained. While control diet-fed dogs had shown deterioration in all 4 measurements, improvements were observed in the test diet-fed dogs. Statistical significance ($P<0.05$) was denoted using an asterisk.

Figure 2:
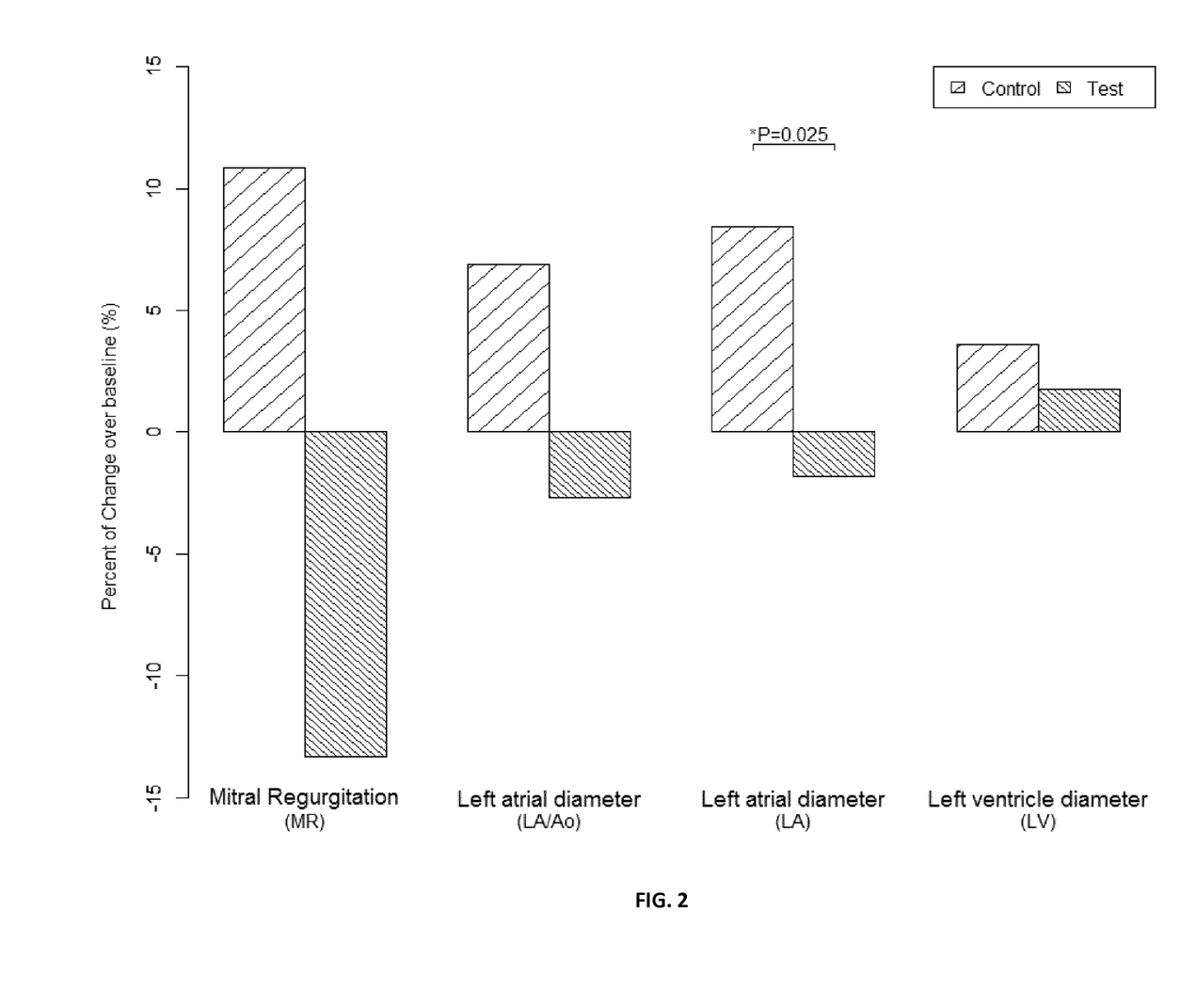
FIG. 2 is a graph of various cardiac measurements for dogs with cardiovascular disease in accordance with one embodiment of the present disclosure.

As shown in FIG. 2, echocardiograms were performed at baseline, 3 months, and 6 months post treatment. Changes between 6 months and baseline in the 4 cardiac measurements, mitral regurgitation grade (MR), left atrial to aortic root ratio (LA/Ao), left atrial diameter (LA), and left ventricular diameter (LV), were calculated. Mann-Whitney U test was performed to compare the differences between dogs fed control diet and dogs fed MCT diet and P values were obtained. While control diet-fed dogs had shown deterioration in all 4 measurements, improvements were observed in the test diet-fed dogs. Statistical significance ($P<0.05$) was denoted using an asterisk.

The data in FIGS. 1-2 demonstrate that while the control diet-fed DMVD dogs showed deterioration in key echocardiographic parameters over the course of the study, the test diet-fed DMVD dogs showed improvements. No significant difference was observed between the dietary groups in healthy dogs.

In addition to the above, serum samples were collected from each dog at baseline and 6 months and were shipped to Metabolon, Inc. (Durham, N.C.) for metabolomics assay (1, 2). The serum concentrations of the following were measured and compared in DMVD dogs fed the control diet (DMVD-CON) and DMVD dogs fed the diet containing Cardiac Protection Blend (DMVD-CPB):

Eicosapentaenoate
Docosahexaenoate
docosapentaenoate
arachidonate
adrenate
docosapentaenoate
mead acid
caprate
margarate
heptadecenoate
oleate/vaccinate
methylpalmitate
oleoylcarnitine
adipolycarnitine
margaroylcarnitine
deoxycarnitine
arginine
citrulline Results are show in FIGS. 3A to 3G, 4A to 4I, 5A to 5B.

Figure 3:
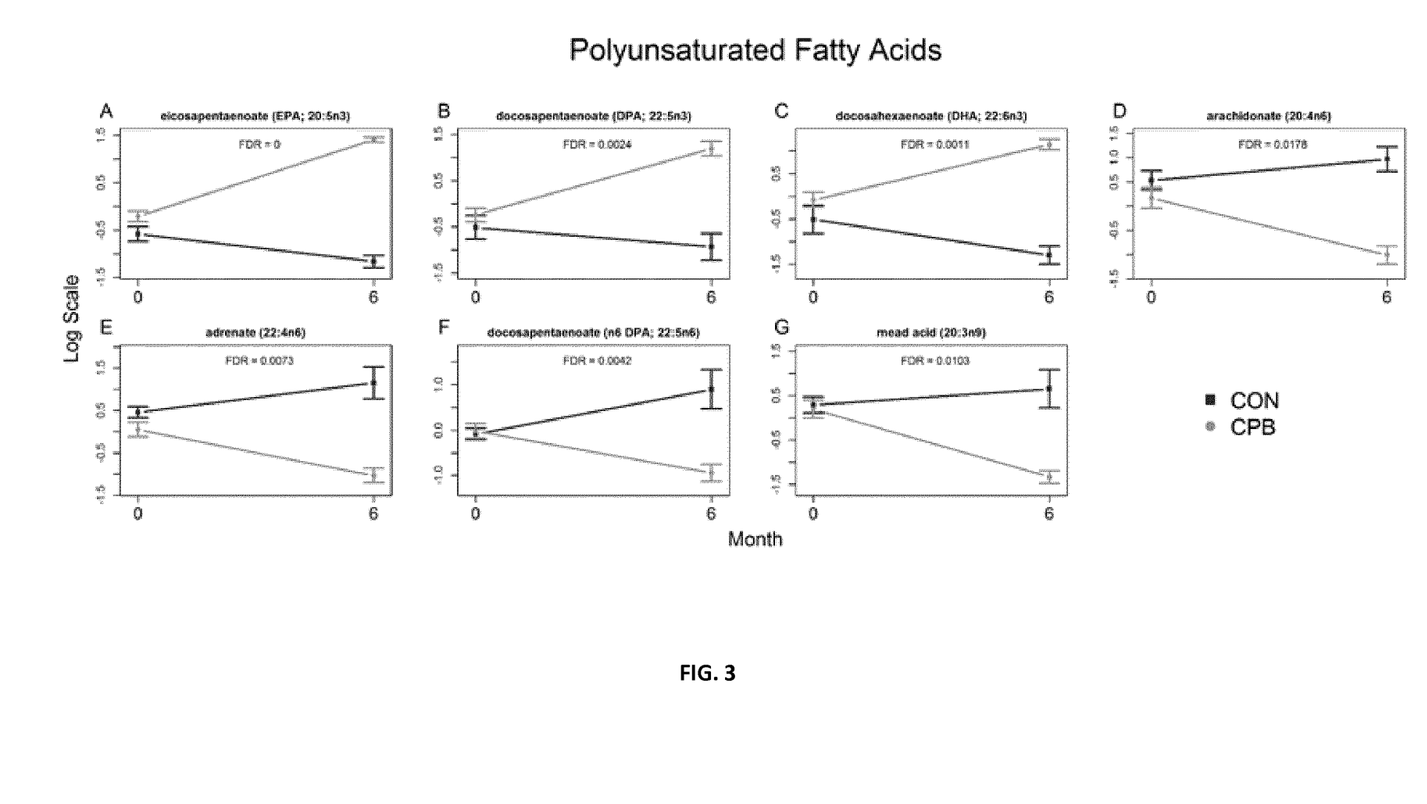
FIG. 3a is a graph showing the measured plasma levels of EPA in dogs fed a composition in accordance with the present disclosure and fed a control.
FIG. 3b is a graph showing the measured plasma levels of omega-3 DPA in dogs fed a composition in accordance with the present disclosure and fed a control.
FIG. 3c is a graph showing the measured plasma levels of DHA in dogs fed a composition in accordance with the present disclosure and fed a control.
FIG. 3d is a graph showing the measured plasma levels of ARA in dogs fed a composition in accordance with the present disclosure and fed a control.
FIG. 3e is a graph showing the measured plasma levels of adrenate in dogs fed a composition in accordance with the present disclosure and fed a control.
FIG. 3f is a graph showing the measured plasma levels of omega-6 DPA in dogs fed a composition in accordance with the present disclosure and fed a control.
FIG. 3g is a graph showing the measured plasma levels of mead acid in dogs fed a composition in accordance with the present disclosure and fed a control.
Figure 4:
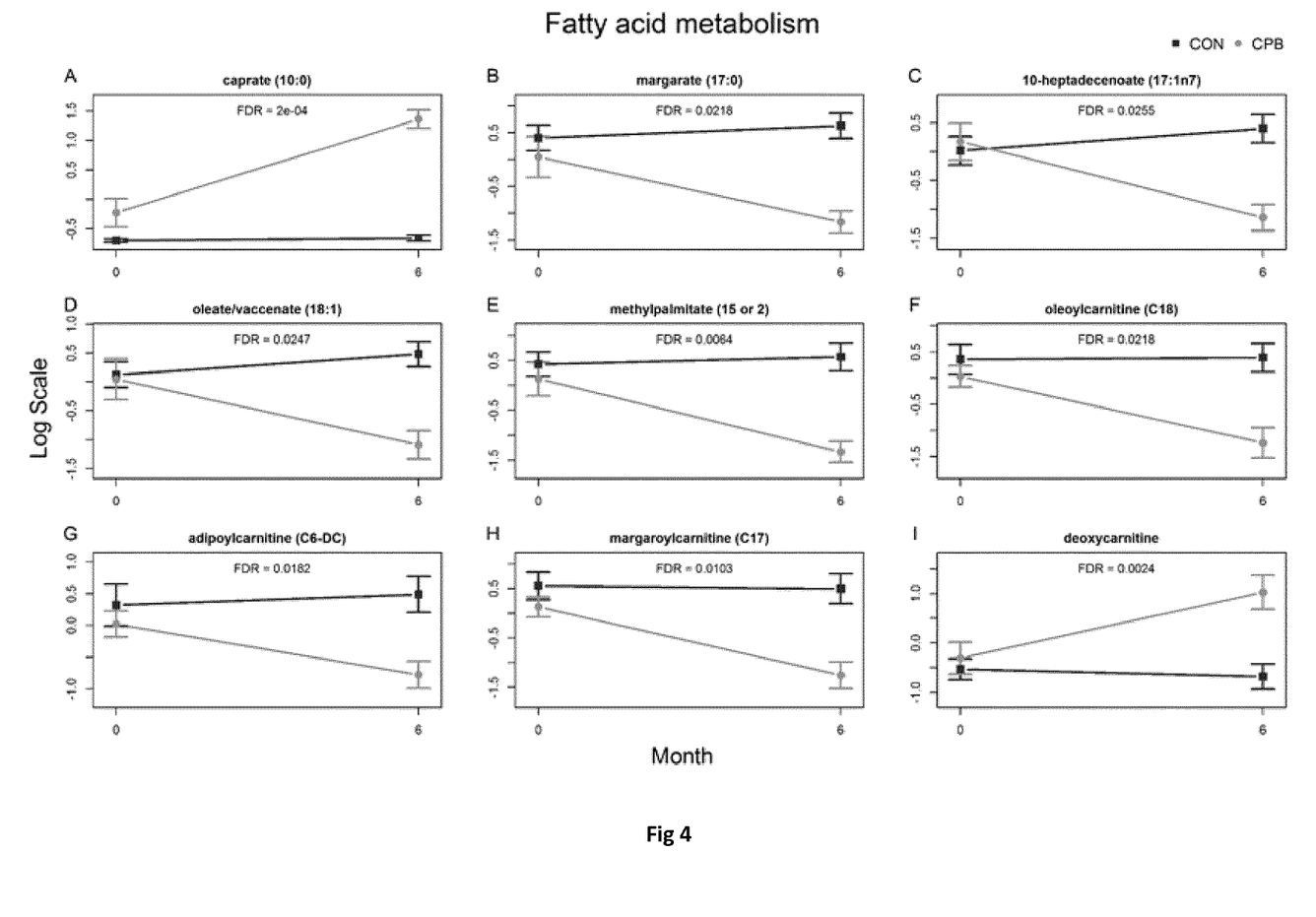
FIG. 4a is a graph showing the measured plasma levels of caprate in dogs fed a composition in accordance with the present disclosure and fed a control.
FIG. 4b is a graph showing the measured plasma levels of margarate in dogs fed a composition in accordance with the present disclosure and fed a control.
FIG. 4c is a graph showing the measured plasma levels of 10-heptadecenoate in dogs fed a composition in accordance with the present disclosure and fed a control.
FIG. 4d is a graph showing the measured plasma levels of oleate/vaccenate in dogs fed a composition in accordance with the present disclosure and fed a control.
FIG. 4e is a graph showing the measured plasma levels of methylpalmitate in dogs fed a composition in accordance with the present disclosure and fed a control.
FIG. 4f is a graph showing the measured plasma levels of oleoylcarnitine in dogs fed a composition in accordance with the present disclosure and fed a control.
FIG. 4g is a graph showing the measured plasma levels of adipolycarnitine in dogs fed a composition in accordance with the present disclosure and fed a control.
FIG. 4h is a graph showing the measured plasma levels of margaroylcarnitine in dogs fed a composition in accordance with the present disclosure and fed a control.
FIG. 4i is a graph showing the measured plasma levels of deoxycarnitine in dogs fed a composition in accordance with the present disclosure and fed a control.

Three omega-3 polyunsaturated fatty acids (PUFAs), eicosapentaenoate (EPA; 20:5n3), docosapentaenoate (DPA; 22:5n3), and docosahexaenoate (DHA; 22:6n3) were upregulated in DMVD-CPB dogs but downregulated in DMVD-CON dogs, when compared to baseline (FIG. 3A-C). In contrast, 3 omega-6 PUFAs, arachidonate (20:4n6), adrenate (22:4n6), docosapentaenoate (n6 DPA; 22:5n6), and one omega-9 mead acid (20:3n9) showed decreases in DMVD-CPB dogs but increases in DMVD-CON dogs (FIG. 3D-G).

Decreases were observed in 3 long chain fatty acids (LCFAs), margarate (17:0), 10-heptadecenoate (17:1n7) and oleate/vaccenate (18:1), and a branched chain fatty acid (BCFA), methylpalmitate (15 or 2), in DMVD-CPB dogs while little increase was found in DMVD-CON dogs when compared to baseline (FIG. 4B-E). In addition, the concentration of deoxycarnitine, the immediate precursor of carnitine biosynthesis, was significantly elevated in DMVD-CPB dogs when compared to baseline (FIG. 4I).

Figure 5:
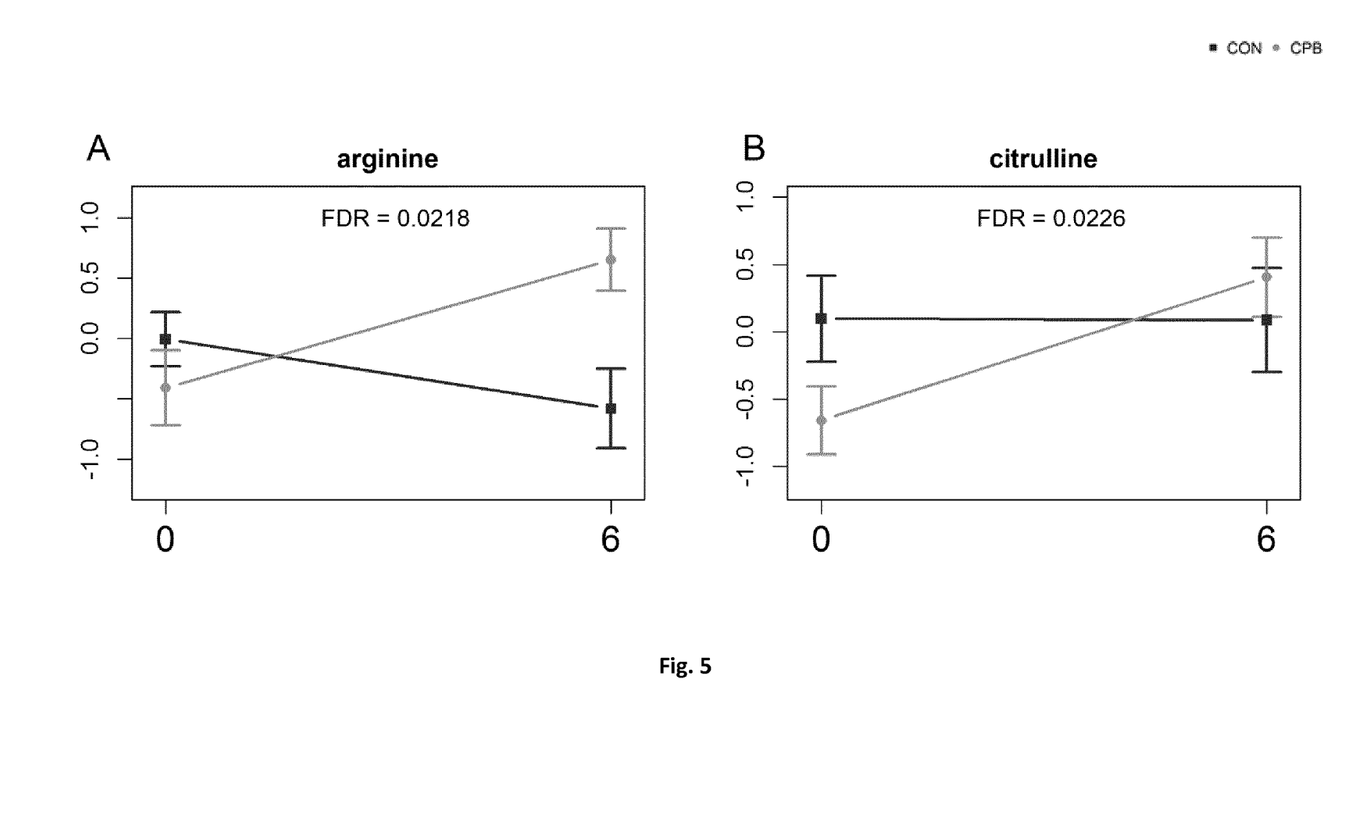
FIG. 5a is a graph showing the measured plasma levels of arginine in dogs fed a composition in accordance with the present disclosure and fed a control.
FIG. 5b is a graph showing the measured plasma levels of citrulline in dogs fed a composition in accordance with the present disclosure and fed a control.

The levels of arginine and citrulline were significantly increased at 6 months in DMVD-CPB dogs while a decrease (arginine) or no change (citrulline) was found in DMVD-CON dogs compared to baseline (FIG. 5A-B).

Repeated measures ANOVA analysis was performed to examine the significance of the diet by time interaction term. A metabolite was considered significant if the adjusted p-value was less than 0.05 for the interaction term. P-values were adjusted for multiple comparisons using false discovery rate. Metabolomics data processing and statistical analysis were performed using MetaboAnalyst 3.0, a comprehensive tool suite for metabolomics data analysis (3-5) and the statistical computing software R (version 3.3.2).

1. Evans A M, DeHaven C D, Barrett T, Mitchell M, Milgram E. Integrated, nontargeted ultrahigh performance liquid chromatography/electrospray ionization tandem mass spectrometry platform for the identification and relative quantification of the small-molecule complement of biological systems. Anal Chem 2009; 81(16): 6656-67. doi: 10.1021/ac901536h.
2. Ohta T, Masutomi N, Tsutsui N, Sakairi T, Mitchell M, Milburn M V, Ryals J A, Beebe K D, Guo L. Untargeted metabolomic profiling as an evaluative tool of fenofibrate-induced toxicology in Fischer 344 male rats. Toxicol Pathol 2009; 37(4):521-35. doi: 10.1177/0192623309336152.

3. Xia J, Mandal R, Sinelnikov I V, Broadhurst D, Wishart D S. MetaboAnalyst 2.0—a comprehensive server for metabolomic data analysis. Nucleic Acids Res 2012; 40(Web Server issue):W127-33. doi: 10.1093/nar/gks374.
4. Xia J, Psychogios N, Young N, Wishart D S. MetaboAnalyst: a web server for metabolomic data analysis and interpretation. Nucleic Acids Res 2009; 37(Web Server issue):W652-60. doi: 10.1093/nar/gkp356.
5. Xia J, Sinelnikov I V, Han B, Wishart D S. MetaboAnalyst 3.0—making metabolomics more meaningful. Nucleic Acids Res 2015; 43(W1):W251-7. doi: 10.1093/nar/gkv380.

Example 2

A nutritional supplement is provided with the following ingredients:

TABLE 1

Composition of Example 1

| Ingredient | Amount per daily dose |
| --- | --- |
| MCT with 53% C8 and 47% C10 fatty acids) | 15 g |
| DHA | 250 mg |
| EPA | 250 mg |
| Lysine | 2 g |
| Methionine | 250 mg |
| Cysteine | 250 mg |
| Magnesium Sulfate | 500 mg |
| Vitamin E | 30 µg |
| Taurine | 250 mg |

The mixture was added to a bluberry muffin mix and baked at 200° c. for 15 mins. The muffin may be for administration in combination with another product comprising MCTs.

The invention claimed is:

1. A method for reduction of risk of or treatment of cardiac enlargement and/or valvular heart disease and/or a condition associated with at least one of the cardiac enlargement or the valvular heart disease in a human subject in need thereof, the method comprising:
orally administering to the human subject a composition comprising one or more medium chain fatty acids each in a form selected from the group consisting of (i) triacylglycerides in which each of the triacylglycerides comprises two or three of the medium chain fatty acids, (ii) monoacylglycerides, (iii) diacylglycerides and (iv) any mixture thereof,
the composition comprising at least 5 wt % of medium chain triglyceride (MCT), at least 0.3 wt % of docosahexaenoic acid (DHA), at least 0.4 wt % of eicosapentaenoic acid (EPA), at least 2 wt % of lysine, at least 2 wt % of methionine and cysteine combined, at least 0.15 wt % of magnesium, at least 0.9 IU/g of vitamin E, and at least 0.2 wt % of taurine, wherein the MCT comprises more than 40% of total C8 and more than 50% of total C10, and
the composition is administered simultaneously, sequentially or separately to a medicine intended to treat and/or reduce the risk of the cardiac enlargement and/or the condition associated therewith and/or a condition that increases the risk of the cardiac enlargement and/or the valvular heart disease in the human subject.

2. The method according to claim 1, wherein the valvular heart disease is selected from the group consisting of mitral valve insufficiency, aortic valve insufficiency, tricuspid valve insufficiency, and combinations thereof.

3. The method according to claim 1, wherein the condition associated with the cardiac enlargement and/or the valvular heart disease is selected from the group consisting of thrombosis, irregular heart rhythms, angina, heart attack, high blood pressure or hypertension, cardiac arrest, heart failure, and combinations thereof.

4. The method according to claim 1, wherein the one or more medium chain fatty acids are selected from the group consisting of C6:0, C8:0, C10:0, C12:0, and combinations thereof.

5. The method according to claim 1, wherein the composition is administered for a period of more than 3 months.

6. The method according to claim 1, wherein the human subject is at risk of the cardiac enlargement and/or the valvular heart disease.

7. The method according to claim 6, wherein the human subject at risk of the cardiac enlargement and/or the valvular heart disease also has a condition selected from the group consisting of high blood pressure, hypertension, hypertrophic cardiomyopathy, heart muscle inflammation, myocarditis, thyroid disease, a disease of the heart valve, a heart attack, a cardiac infarction, and combinations thereof.

8. The method according to claim 7, wherein the cardiac enlargement or the valvular heart disease is age-related.

9. The method according to claim 1, wherein the human subject is a human adult.

10. The method according to claim 1, wherein the composition further comprises carnitine.

11. The method according to claim 1, wherein the composition is a product selected from the group consisting of a medicament, a food product, a medical food, an oral nutritional supplement, a nutritional composition and a supplement to a food product.

12. The method according to claim 1, wherein the composition further comprises one or more additional triglycerides in which less than three fatty acids of each of the one or more additional triglycerides is a medium chain fatty acid.

13. The method according to claim 1, wherein the composition is a food product selected from the group consisting of a health drink, a ready-made drink, a soft drink, a juice, a milk-shake, a yogurt drink, a smoothie, a soy-based drink, a bar, and combinations thereof.

14. A composition comprising one or more medium chain fatty acids each in a form selected from the group consisting of (i) triacylglycerides in which each of the triacylglycerides comprises two or three of the medium chain fatty acids, (ii) monoacylglycerides, (iii) diacylglycerides and (iv) any mixture thereof,
the composition comprising at least 5 wt % of medium chain triglyceride (MCT), at least 0.3 wt % of DHA, at least 0.4 wt % of EPA, at least 2 wt % of lysine, at least 2 wt % of methionine and cysteine combined, at least 0.15 wt % of magnesium, at least 0.9 IU/g of vitamin E, and at least 0.2% of taurine, wherein the MCT comprises more than 40% of total C8 and more than 50% of total C10, and
the composition is formulated designed to be orally administered to a human subject simultaneously, sequentially or separately to a medicine intended to treat and/or reduce the risk of the cardiac enlargement and/or the condition associated therewith and/or a condition that increases the risk of the cardiac enlargement and/or the valvular heart disease in the human subject.

15. The composition according to claim 14, wherein the composition is selected from the group consisting of a medicament, a food product, a medical food, an oral nutritional supplement, a nutritional composition and a supplement to a food product.

16. The composition according to claim 14, wherein the composition is a food product selected from the group consisting of a health drink, a ready-made drink, a soft drink, a juice, a milk-shake, a yogurt drink, a smoothie, a soy-based drink, a bar, and combinations thereof.

\* \* \* \* \*